(12) United States Patent
Suga et al.

(10) Patent No.: US 7,001,723 B1
(45) Date of Patent: Feb. 21, 2006

(54) CATALYTIC RNAS WITH AMINOACYLATION ACTIVITY

(75) Inventors: Hiroaki Suga, Williamsville, NY (US); Dimitrios Kourouklis, Williamsville, NY (US); Hirohide Saito, Buffalo, NY (US); Nick Lee, Snyder, NY (US); Neil Bonzagni, Buffalo, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 452 days.

(21) Appl. No.: 09/721,414

(22) Filed: Nov. 22, 2000

Related U.S. Application Data

(60) Provisional application No. 60/167,331, filed on Nov. 24, 1999, provisional application No. 60/214,382, filed on Jun. 28, 2000.

(51) Int. Cl.
  *C12Q 1/68*     (2006.01)
  *C07H 21/04*    (2006.01)
(52) U.S. Cl. .......................... 435/6; 435/91.1; 435/325; 435/375; 536/23.1; 536/24.5
(58) Field of Classification Search ................ 514/44; 435/6, 325, 375, 91.1; 536/23.1, 24.5, 91.1
See application file for complete search history.

(56) References Cited

U.S. PATENT DOCUMENTS

| | | | |
|---|---|---|---|
| 5,270,163 A | 12/1993 | Gold et al. | 435/6 |
| 5,475,096 A | 12/1995 | Gold et al. | 536/23.1 |
| 5,871,924 A | 2/1999 | Yarus et al. | |
| 5,990,142 A | 11/1999 | Carganico et al. | 514/382 |
| 5,998,142 A | 12/1999 | Gold et al. | 435/6 |
| 6,063,566 A | 5/2000 | Joyce | 435/6 |

FOREIGN PATENT DOCUMENTS

WO  WO 99/36517  7/1999

OTHER PUBLICATIONS

Tinoco et al., J. Mol. Biol. (1999) 293, 271-281.*
Beaudry et al., "Directed Evolution of An RNA Enzyme", *Science*, Jul. 31, 1992, v 257, n 5070, p635.
Piccirilli et al., "Aminoacyl Esterase Activity of The Tetrahymena Ribozyme", *Science*, Jun. 5, 1992, v 256, n 5062, p1420-1424.
Pan et al., "In Vitro Selection of RNAs That Undergo Autolytic Clevage with $Pb^{2+}$", *Biochemistry*, Apr. 28, 1992 v 31, n 16, p3887-3895.
Bartel et al., "Isolation on New Ribozymes From A Large Pool of Random Sequences", *Science*, Sep. 10, 1993 vol. 261(5127), pp. 1411-1418.
Schultz et al., "Expanding The Scope of RNA Catalysis", *Science*, Jun. 24, 1994, vol. 264(5167), pp. 1924-1927.
Lorsch et al., "In Vitro Evolution of New Ribozymes With Polynucleotide Kinase Activity", *Nature*, vol. 371: Sep. 1, 1994, p. 31-36.
Brenner et al., "Encoded Combinatorial Chemistry", *Proc. Natl. Acad. Sci. USA*, 1992, vol. 89: pp. 5381-5383.
Illangasekare et al., "Aminoacyl-RNA Synthesis Ctalyzed by an RNA", *Science*: vol. 267(5198); Feb. 3, 1995; pp. 643-646.
Lohse et al., "Ribozyme-catalysed amino-acid transfer reactions", *Nature*, May 30, 1996, vol. 381(6581) p 442-444.
Suga t al., "Structural and Kinetic Characterization of an Acyl Transferase Ribozyme", 1998, *J. Am. Chem. Soc.*, v 120, p 1151-1156.
Illangasekare, M. et al., Specific, rapid synthesis of Phe-RNA by RNA, Proceedings of the National Academy of Sciences of the United States of America, May 11, 1999, vol. 96, No. 10, pp. 5470-5475.
Lee, N. et al., Ribozyme-Catalyzed TRNA Aminoacylation, Nature Structural Biology, New York, NY, US, vol. 7, No. 1, Jan. 2000, pp. 28-33.
Schimmel, P. et al., Exiting an RNA world, Nature Structural Biology, Jan. 2000, vol. 7, No. 1, pp. 5-7.
Jenne, et al., A novel ribozyme with ester transferase activity, Chemistry & Biology 1998, vol. 5, No. 1, p. 23-34.
Lee, et al., "Ribozyme-Catalyzed TRNA Aminoacylation", Nature Structural Biology, New York, NY, vol. 7, No. 1, Jan. 2000, p. 28-33, XP002939339 ISSN: 1072-8368.
Schimmel, et al.,, "Exiting an RNA world.", Nature Structural Biology, Jan. 2000, vol. 7, No. 1, Jan. 2000, p. 5-7, XP002305387, ISSN: 1072-8368.
Illangasekare, et al., Specific, rapid synthesis of Phe-RNA by RNA, Proc. Natl. Acad. Sci. USA, vol. 96, May 1999, p. 5470-5475.
Fechter, et al. Ribozyme Processed tRNA Transcripts With Unfriendly Internal Promoter for T7 RNA Polymerase: Production and Activity. FEBS Letters 436 pp. 99-103 (1998).
Illangasekare, et al. Small-Molecule-Substrate Interactions With a Self-Aminoacylating Ribozyme. J. Mol. Biol. 268, pp. 631-639 (1997).
Illangasekare, et al., Specific, Rapid Synthesis of Phe-RNA by RNA Proc. Natl. Acad. Sci. USA, vol., 96 pp. 5470-5475 (May, 1999).

* cited by examiner

*Primary Examiner*—Sean McGarry
*Assistant Examiner*—J D Schultz
(74) *Attorney, Agent, or Firm*—Hodgson Russ LLP

(57) ABSTRACT

The present invention provides catalytic RNA molecules having cis or trans aminoacylation activity. The catalytic RNA molecules having cis aminoacylation activity comprise a catalytic domain and an aminoacylation domain. The catalytic RNA molecules having trans aminoacylation activity only have the catalytic domain. A method is provided for constructing and screening of these molecules. These molecules are suitable for aminoacylating tRNA-like molecules with specific amino acids.

9 Claims, 5 Drawing Sheets

CATALYTIC RNAS WITH AMINOACYLATION ACTIVITY

This application claims the priority of U.S. provisional application No. 60/167,331 filed on Nov. 24, 1999 and U.S. provisional application No. 60/214,382 filed on Jun. 28, 2000, the disclosure of which are incorporated herein by reference.

FIELD OF THE INVENTION

The present invention relates generally to the field of catalytic RNA molecules, and more particularly to catalytic RNA molecules having the ability to aminoacylate tRNA-like molecules in cis or in trans.

BACKGROUND OF THE INVENTION

Proteins containing non-natural amino acids hold great promise for biomedical and therapeutic purposes. Such amino acids may be particularly useful in the structural and functional probing of proteins, construction of peptide libraries for combinatorial chemistry, and in proteomics. However, the synthesis of such proteins has not heretofore been easy. In the translation system that is known to occur currently in nature, genetic coding is carried out by aminoacyl tRNA synthetases (ARSs). They exist in 20 different forms, each of which specifically catalyzes the esterification of a single amino acid to its cognate tRNA isoacceptor, thereby directly connecting the amino acid with its corresponding anticodon triplet. Because misacylation of non-cognate amino acids to tRNAs causes misincorporation of amino acids into cellular proteins which can be fatal to their intracellular activity, the fidelity of the aminoacylation reactions by the ARSs must be extremely high. To achieve this important task, the ARSs use very sophisticated mechanisms to selectively recognize the cognate amino acids and tRNAs. The recognition determinants of tRNAs are diverse ranging from the anticodon loop to the acceptor-Ti~C stem and the phosphate-ribose backbone. Because of these complexities, engineering of ARSs with desired specificities toward non-natural tRNAs and amino acids has not been achieved. As a result attention has turned to the nucleic acids.

For many years, nucleic acids were considered to be only informational molecules. However, the pioneering work of Cech and coworkers (Cech, 1987, Science, 236:1532–1539; McCorkle et al., 1987, Concepts Biochem. 64:221–226) demonstrated the presence of naturally occurring RNAs that can act as catalysts (ribozymes). However, although these natural RNA catalysts have only been shown to act on ribonucleic acid substrates for cleavage and splicing, recent development of artificial evolution of ribozymes has expanded the repertoire of catalysis to various chemical reactions. For example, RNAs have been reported to catalyze phosphodiester cleavage on DNA (Beaudry et al., 1992, Science, 257:635), hydrolysis of aminoacyl esters (Piccirilli et al., 1992, Science, 256:1420–1424), self-cleavage (Pan et al., 1992, Biochemistry, 31:3887), ligation of an oligonucleotide with a 3'OH to the 5' triphosphate end of the catalyst (Bartel et al., 1993, Science, 261:1411–1418), biphenyl isomerase activity (Schultz et al., 1994, Science, 264:1924–1927), and polynucleotide kinase activity (Lorsch et al., 1994, Nature, 371:31–36).

To identify novel catalysts, Brennen et al. (1992, Proc. Natl. Acad. Sci., USA, 89:5381–5383) constructed a heterogenous pool of macromolecules and used an in vitro selection process to isolate molecules that catalyze the desired reaction. A variation of this approach has been used by Gold et al. (U.S. Pat. No. 5,475,096). This method, known as Systematic Evolution of Ligands by Exponential enrichment (SELEX), identifies nucleic acids that have the ability to form specific, non-covalent interactions with a variety of target molecules. A related patent (U.S. Pat. No. 5,990,142) is based on the SELEX method, but can potentially identify modified and non-modified RNA molecules that can catalyze covalent bond formation with a target. Recently, a similar approach was used to identify catalytic RNA molecules having phosphodiesterase, amidase activity (U.S. Pat. No. 6,063,566 to Joyce).

Additionally, studies have identified RNA molecules that can catalyze aminoacyl-RNA bonds on their own (2')3'-termini. (Illangakekare et al., 1995 Science 267:643–647), or where an RNA molecule can transfer an amino acid from one RNA molecule to another (Lohse et al., 1996, Nature 381:442–444).

However, there has been no demonstration heretofore of catalytic tRNA-like molecules that can cause aminoacylation of RNA molecules which are physiologically significant in modern protein translation processes.

SUMMARY OF THE INVENTION

The present invention provides catalytic RNAs with cis-aminoacylation activity. The catalytic RNAs comprise a tRNA-like domain and a ribozyme domain. The ribozyme domain has the catalytic activity and also confers amino acid specificity for aminoacylation. Thus, these catalytic RNAs have the ability to selectively aminoacylate their own 3'-termini with specific amino acids (termed herein as cis-aminoacylating RNA molecules). These catalytic RNAs can be used to aminoacylate tRNA-like sequences that are not naturally aminoacylated.

The present invention also provides catalytic RNA molecules that can aminoacylate tRNA-like molecules in trans (termed herein as trans-aminoacylating RNA molecules). The trans-aminoacylating RNAs correspond to the ribozyme domain of the cis-aminoacylating RNAs. These catalytic RNA molecules can be used to aminoacylate tRNA-like molecules with desired natural or non-natural amino acid in trans.

The present invention also provides a method of constructing self-aminoacylating RNA molecules. This method comprises the steps of attaching a sequence to the 5' end of a tRNA-like molecule, said sequence comprising a ribozyme sequence. This method can be used to generate catalytic RNAs that can catalyze the aminoacylation of their own 31 ends. These catalytic molecules can be cleaved by RNase P to produce a different species of catalytic RNA molecules which have the ability to aminoacylate tRNA-like molecules in trans.

The present invention also provides a method for the identification of RNA sequences having aminoacylation activity. The method comprises the steps of providing a pool of RNA sequences having a tRNA-like domain and a ribozyme domain, contacting the RNA sequences of the pool with the desired natural or non-natural amino acid, partitioning the aminoacylated RNA molecules from the non aminoacylated molecules, amplifying and sequencing the aminoacylated RNA molecules.

The present invention also provides a method for aminoacylating the self-aminoacylating catalytic molecules provided herein. The method comprises the steps of providing RNA molecules having the catalytic activity of self aminoacylating, contacting the RNA molecules with the desired natural or non-natural amino acid, and isolating the aminoacyated RNA molecules.

The present invention also provides a method for aminoacylating tRNA-like molecules. The method comprises the steps of providing a catalytic RNA molecule having a trans-aminoacylating activity, contacting the RNA molecule with a tRNA-like molecule and the desired amino acid, and isolating the aminoacylated RNA molecules.

DETAILED DESCRIPTION OF THE INVENTION

Figure 1A:
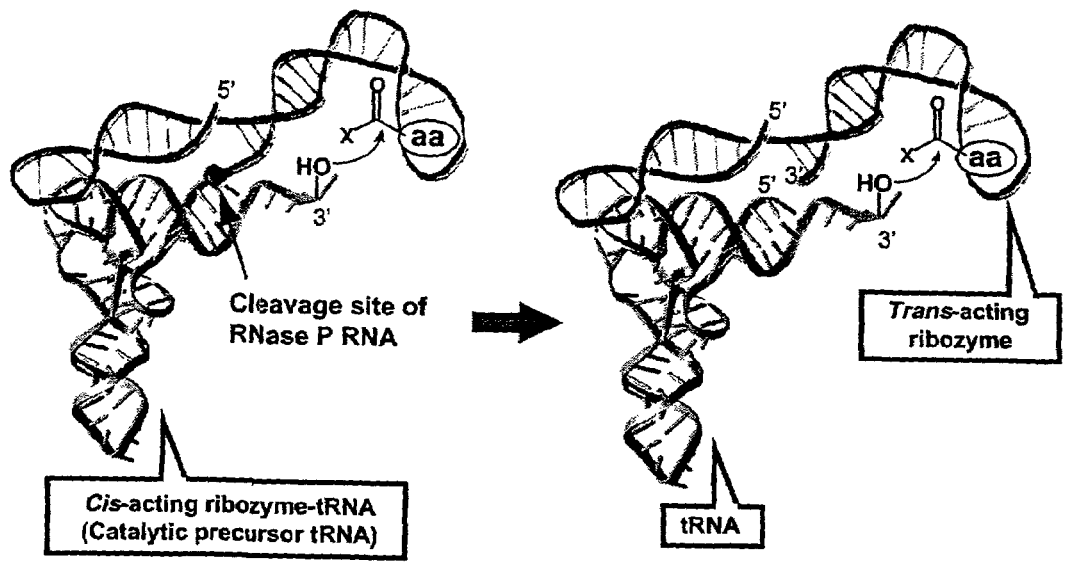
FIG. 1A is a schematic representation of a catalytic RNA with self-aminoacylation activity (left) and a catalytic RNA with trans-aminoacylation activity (right). The amino acid substrate (the amino acid side chain and leaving group are shown with aa and X, respectively) binds to the 5'-leader ribozyme domain, and the nucleophilic attack of the tRNA 3'-hydroxyl (indicated by a curved arrow) is accelerated. The cleavage site of RNase P RNA is shown by the straight arrow.

The phrase "tRNA-like molecules" or "tRNA-like domains" or "tRNA-like sequences" as used herein for the purposes of specification and claims, means RNA molecules that have sequences consistent with the formation of a cloverleaf structure typically associated with tRNAs. An example of a tRNA-like molecule is otRNA (SEQ ID NO:18). Other t-RNA-like molecules are the tRNA domains of SEQ ID NO:5–15 i.e., nucleotides 86–146 of SEQ ID NO:5, nucleotides 90–151 of SEQ ID NO:6, nucleotides 90–150 of SEQ ID NO:7, nucleotides 89–150 of SEQ ID NO:8, nucleotides 90–150 of SEQ ID NO:9, nucleotides 89–149 of SEQ ID NO:10, nucleotides 89–149 of SEQ ID NO:11, nucleotides 89–149 of SEQ ID NO:12, nucleotides 89–149 of SEQ ID NO:13, nucleotides 90–150 of SEQ ID NO:14, and nucleotides 89–148 of SEQ ID NO:15. Still other tRNA-like molecules are SEQ ID NO:20–22.

The phrase "ribozyme" as used herein for the purposes of specification and claims, means an RNA molecule that is capable of catalyzing a chemical reaction.

The phrase "natural amino acid" refers to any amino acid among the twenty amino acids that are normally aminoacylated onto tRNAs in living cells. Such amino acids are alanine, valine, leucine, isoleucine, proline, tryptophan, phenylalanine, methionine, glycine, serine, threonine, tyrosine, cysteine, glutamine, asparagine, lysine, arginine, histidine, aspartic acid, and glutamic acid. Consequently, the phrase "non-natural amino acids" means any amino acid other than the natural amino acids or modification of a natural amino acid.

The term "cis" means within the same molecule. The term "trans" means on or to a different molecule.

The term "5'-leader domain" or "catatlytic domain" or "5'-leader ribozyme" means the 5' region of the catalytic molecules having cis-aminoacylating activity. Examples of such 5'-leader domains are nucleotides 1–85 of SEQ ID NO:5, nucleotides 1–89 of SEQ ID NO:6, nucleotides 1–89 of SEQ ID NO:7, nucleotides 1–88 of SEQ ID NO:8, nucleotides 89 of SEQ ID NO:9, nucleotides 1–88 of SEQ ID NO:10, nucleotides 1–88 of SEQ ID NO:11, nucleotides 1–88 of SEQ ID NO:12, nucleotides 1–88 of SEQ ID NO:13, nucleotides 1–89 of SEQ ID NO:14 and nucleotide 1–88 of SEQ ID NO:15.

The present invention is directed to catalytic RNA molecules that can catalyze aminoacylation reactions. The catalytic RNA molecule having self-aminoacylating activity has two domains, a catalytic domain and an aminoacyl acceptor domain. The catalytic domain contains a sequence which has ribozymal activity. This domain alos confers amino acid specifity.

To construct the catalytic RNA molecules having self aminoacylation activity, a selection process is used on a randomly synthesized RNA pool. By attaching the RNA molecules of this pool to the 5' end of a tRNA-like molecule and contacting the complex with a substrate molecule (natural or non-natural amino acid), self-aminoacylating RNA molecules are identified. These molecules can then be selectively amplified. The self-aminoacylating nature of these molecules can be confirmed by standard assays such as mobility-gel-shift assays. To facilitate the isolation of the active aminoacylated RNA species, a biotin tag may be attached to the target molecule. Alternatively, a water soluble form of biotin may be used to label the aminoacylated RNAs subsequent to generation of the aminoacylated RNA species. These biotin labeled species can be isolated by using strepavidin coated agarose. Repeated rounds of selective amplification yield pure species of the catalytic RNA with self aminoacylating activity. A round of selection comprises in part reverse-transcribing RNAs collected from the SAv bound portion of the reaction in order to produce cDNAs. The cDNAs are subjected to the polymerase chain reaction (PCR) followed by transcription of the PCR products to generate RNAs used in the next round of selection. The RNAs obtained from the final selection round are subjected to mobility gel-shift assays to demonstrate self-aminoacylation and trans-aminoacylation activity.

The catalytic molecules of the present invention can also aminoacylate RNA species in trans. To produce such catalytic molecules, the aminoaccyl acceptor domain (the tRNA-like domain) can be cleaved from the catalytic domain by bacterial RNase P digestion. The catalytic domain is able to aminoacylate the aminoacyl acceptor domain or a tRNA-like molecule in trans. The catalytic molecules can also be synthesized by in vitro run-off transcription catalyzed by an appropriate RNA polymerase from the corresponding DNA templates by methods known to those skilled in the art.

The aminoacyl acceptor domain is a tRNA-like molecule. A suitable example of a tRNA-like molecule is an artificial orthogonal suppressor tRNA (otRNA see FIG. 1B). Alternatively, an amber supressor tRNA derived or isolated from different species, such as human, can be used for this purpose. This tRNA sequence is derived from an amber suppressor tRNAG$^{Gln2}$ but is not recognized by bacterial ARSs. The otRNA can be attached to unique catalytic domains that confer aminoacylation activity and amino acid specificity.

Once sequences known to possess aminoacylating activity are isolated, they can be used in a scaffold-based approach to isolating additional aminoacylating sequences. The pre-24$^{Phe}$ sequence region (except for the 5'-primer sequence) in DNA form is randomly mutagenized such that each base has a certain percentage chance of being non-wild-type. This DNA pool is then annealed with the anistense DNA of the otRNA, and the annealed pool is extended to full-length duplex DNA. New copies of the templates are generated by PCR, these are transcribed and subject to selection as previously described.

Taking advantage of the catalytic scaffold of the pre-24' allows screening of a focused sequence space in which most sequences can maintain the secondary or even tertiary structures of the pre-24 Phe Despite this narrowed focus, the scaffold pool has enough random mutations to give the desired alteration of amino acid specificity dependant upon the amino-acid chosen to be the amino acid component of the substrate. Therefore, the likelihood of encountering active sequences can become higher than the selection using a completely random pool. For the scaffolding pool, it is unnecessary to deal with a high complexity pool because fewer nucleotides are randomized (depending upon the mutation rate, its complexity can be two or three orders of magnitude lower). Therefore, the selection is much less labor-intensive and the outcome can be obtained more rapidly.

These and other embodiments will become more clear from the examples described below, which are to be construed as illustrative and not limiting.

EXAMPLE 1

This embodiment describes the construction of a pool of RNA molecules for screening of aminoacylation activity. In an illustration of this embodiment, randomized sequences were generated, attached to a tRNA-like molecule. Thus, a random pool of 70 nucleotides was attached to the 5' end of a tRNA-like molecule (otRNA) as follows.

Pool construction: Four synthetic oligonucleotides were used for the pool construction: the random pool DNA template (5'-GGATCGTCAGTGCATTGAGA-N70-GGTG-GTATCCCCAAGGGGTA-3')(SEQ ID No. 1), the DNA template complementary to the orthogonal tRNA (otRNA) (SEQ ID No. 2), the 5'-primer containing T7 promoter sequence (SEQ ID No. 3), and 3'-primer (SEQ ID No. 4) A large-scale Taq DNA polymerase- extension of the DNA templates was performed under thermocylcing conditions (95° C. for 10 min, 55° C. for 10 min, and 72° C. for 10 min). The full-length product was then amplified by seven cycles of large-scale PCR in the presence of the 5'- and 31-primers. Four equivalents of the pool DNA with an approximately $10^{15}$ complexity were transcribed by T7 RNA polymerase in the presence of a-[$^{32}$P]-UTP, and purified by 6% polyacrylamide gel electrophoresis (PAGE).

EXAMPLE 2

This embodiment describes the selection of active sequences from the RNA molecules constructed in Example 1. As illustrations, the following substrates were used to select aminoacylating species of RNA.

Substrates

N-biotinyl-L-aminoacyl-cyanomethyl esters (Biotin-aa-CME) were chosen as the aminoacyl donor substrates because the CME group has a balance of activation and hydrolytic stability. Furthermore, CME has no hydrogen-bonding functionalities, which helps to ensure that the primary interaction with RNA will occur through the amino acid side chain of the substrate.

Other substrates included Pheylalanyl adneylate (Phe-AMP) and pheylalanyl thioester (Phe-TE). These substrates were also chosen for reasons described above and to demonstrate specificity to the amino acid rather than other components of the substrate. The biotin tag facilitates the isolation of active, i.e. aminoacylated, sequences on immobilized streptavidin (SAv) agarose via an interaction between the biotin moiety of the substrate and the SAv. N-biotinyl-L-phenylalanyl-cyanomethyl esters (Biotin-Phe-CME) and Boc-Phe-CME (Boc is tert-butoxy carbonyl) were synthesized essentially by the procedure as previously described (Suga, et al. *J. Am. Chem. Soc.* 120: 1151–1156 1998). Synthesis of Phe-CME was carried out as follows: 9:1 TFA/anisole solution (500 mL) was added to Boc-Phe-CME (385 mg, 1.26 mmol) under argon atmosphere and the mixture was stirred at room temperature for 30 min. The solvent was removed in vacuo and ca. 4 M hydrogen chloride in dioxane (4 mL) was added to the residue. The solution was concentrated in vacuo, and the addition of anhydrous ether to the residue yielded precipitate. The precipitate was dissolved in a minimal amount of MeOH, and to this solution anhydrous ether was added to reprecipitate the product. Purity of the product was determined using nuclear magnetic resonance (NMR).

Synthesis of phenylalanyl adenylate (Phe-AMP) was carried out essentially as described previously (Berget al. *Bio. Chem.* 253: 608–611, 1958). $^{32}P$ NMR analysis of the product indicated that the purity of Phe-AMP was approximately 50' and the remaining side-product was unreacted AMP. The product was dissolved in water, and used for aminoacylation without further purification.

Synthesis of phenylalanyl thioester (Phe-TE) was as follows: N,N-bis[2-oxo-3-oxozolidiyl]phosphordiamitic chloride (238 mg, 0.94 mmol) was added to a solution of Boc-Phe (307 mg, 1.16 mmol) and triethylamine (175 mL, 2.26 mmol) in $CH_2Cl_2$ (10 mL). To this mixture, ethyl 2-mercapto acetate (100 mL, 0.91 mmol) was slowly added, and the reaction mixture was then stirred vigorously for 5 h at room temperature. The reaction was quenched by the addition of 20% $NaHCO_3$ aqueous solution. After standard aqueous work-up, Boc-Phe-TE was isolated by column chromatography. 9:1 TFA/anisole solution (500 mL) was added to Boc-Phe-TE (200 mg, 0.30 mmol) under argon atmosphere, and the mixture was stirred at room temperature for 30 min. The solvent was removed in vacuo and ca. 4M hydrogen chloride in dioxane (4 mL) was added to form the hydrochloride salt. The solution was concentrated in vacuo, and the residue was dissolved in ether. The addition of petroleum ether to this solution resulted in the formation of precipitate, which was rinsed with ether and filtered to yield Phe-TE.

Selection of Active Sequences

Selection reactions were carried out under the following conditions: A mixture of 10 $\mu$M (first round only) or 1 $\mu$M RNA pool, 1 mM Biotin-Phe-CME, in an EK buffer (50 mM EPPS, 500 mM KCl, pH 7.5), 100 $\mu$M $MgCl_2$ and ethanol (25% of the total volume) The pool RNA was preincubated in the EK buffer, heated at 95° C. for 5 min, and cooled to 25° C. over 5 min. $MgCl_2$ was then added followed by a 5 min equilibration. The reaction was initiated by the addition of the substrate solution in ethanol, and incubated for 3 h at 25° C. (30 min in the 15–17th rounds). The reaction was stopped by adding 2 volumes of cold ethanol, and the RNA was ethanol-precipitated twice. The RNA pellet was dissolved into EKE buffer (50 mM EPPS, 500 mM KCl, 5 mM EDTA, pH 7.5), then incubated with 200 $\mu$L (1 mL for the first round) of streptavidin agarose for 30 min at room temperature. Unbound RNAs were eluted with 20-resin volumes of the EKE buffer, 40-resin volumes of 4 M urea, then 10-resin volumes of water. The resin-bound RNAs were eluted by heating at 95° C. for 10 min in the presence of 10 mM biotin at pH 7. The collected RNAs were reverse-transcribed using 100 units M-MLV reverse transcriptase (Promega™) in the presence of 1 $\mu$M 3' primer (SEQ ID No. 4), 125 $\mu$M dNTPs, 50 mM Tris-HCl, 75 mM KCl, 3 MM $MgCl_2$, 10 mM DTT, pH 8.3 at 42° C. for 1 h (for 1–14 rounds) or 10 min (for 15–17 rounds). The cDNAs were subjected to PCR followed by transcription under standard conditions.

Figure 2:
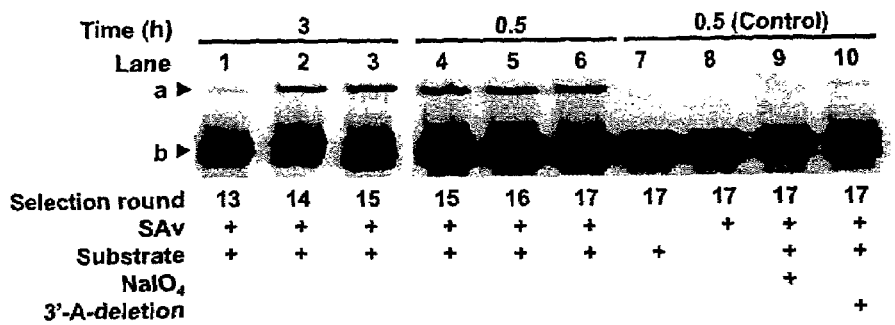
FIG. 2 is a representation of an autoradiogram showing self-aminoacylation activity as a function of selection cycle. a, Biotin-Phe-RNA complexed with SAv; b, RNA pool.

Fifteen rounds of selective amplification of self-aminoacylating RNA molecules in the pool yielded an enrichment of active sequences, which was confirmed by a SAv-dependent mobility-gel-shift assays (FIG. 2, lanes 1–3). Approximately 10% of the total input RNA molecules from round 15 showed aminoacylation after 3 h (lane 3). Two rounds of selection with shorter incubation times were employed in order to further enhance the activity in the pool (lanes 4–6). The absence of SAv or substrate resulted in loss of the retarded band (lanes 7,8), indicating that self-aminoacylation of active RNAs with the Biotin-Phe group is occurring. Periodate oxidation of the 3' terminal diol or deletion of the 3' adenosine resulted in near complete inhibition of aminoacylation (lanes 9,10), strongly suggesting that the 3' terminal hydroxyl group is the aminoacylation site.

Figure 3:
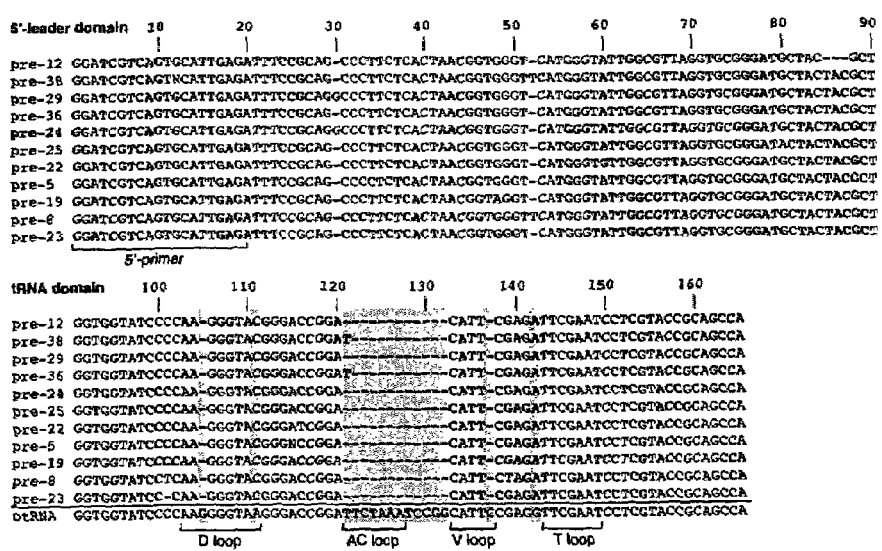
FIG. 3 is a representation of the sequence alignment of active clones isolated from round 17 RNA. For the alignment of the tRNA domain, the wild-type otRNA is shown together with the selected rtRNA sequences. Consensus deletions and mutations appearing in the tRNA domain are highlighted by boxes. The abbreviations for tRNA loops are: AC, anticodon; V, variable; T, T C.

Thirty-six individual clones form the round 17 pool were were screened for self-aminoacylation (self aminoacylation assay described in Example B), and 11 clones exhibited appreciable activity (SEQ ID NO:5–15). Alignment of their sequences revealed an approximately 95% identity in the 5' leader domains (FIG. 3, top). A representative clone, termed as the pre-24 or rtRNA (SEQ ID NO:9), was selected for confirmation of the self-aminoacylation activity.

EXAMPLE 3

The self-aminoacylation activity of pre-24 in the presence of Biotin-Phe-CME was assayed under conditions similar to those of the selection except that 12.5 mM KCl and 5% ethanol were used. At each time point, an aliquot of the reaction was ethanol-precipitated twice, and the pellet was dissolved into 7 $\mu$L a MEUS buffer (25 mM MOPS, 5 mM EDTA, 8 M Urea, 10 $\mu$M streptavidin, pH 6.5). The reactions were carried out in the presence of 1 $\mu$M RNA and 1 mM Biotin-Phe-CME (FIG. 4, lanes 1, 2, 4, and 5) or 1 mM Biotin-aa-CME (lanes 6–10) or in the absence of substrate (lane 3). For periodate oxidation (lane 4), pre-24 was treated with 10 mM NaOH at 0° C. for 1 h and ethanol-precipitated prior to the aminoacylation reaction. The reactions were incubated for 30 min (lanes 1–4) or 2 h (lanes 5–10). The resulting solution was analyzed by 10% PAGE in a cold room in order to keep the gel temperature below 20° C. (FIG. 4). A plot of initial rates vs. substrate concentration revealed Michaelis-Menten behavior with kinetic parameters of $k_{cat}$=0.10+0.01 min$^{-1}$ and Km=6.3±1.2 mM, while the solubility limit of substrate constrains its actual working concentration to below 5 mM. The background rate was determined by incubating otRNA with 1 mM Biotin-Phe-CME for 3 h in the same reaction buffer as above, giving a yield of 0.01% of the aminoacyl-otRNA (lane 11). The background rate is thus estimated to be an approximately 5.5×10$^{-7}$ Min$^{-1}$. The observed rate acceleration by ribozyme is approximately 10$^5$-fold greater than background.

Figures 4A, 4B, 4C:
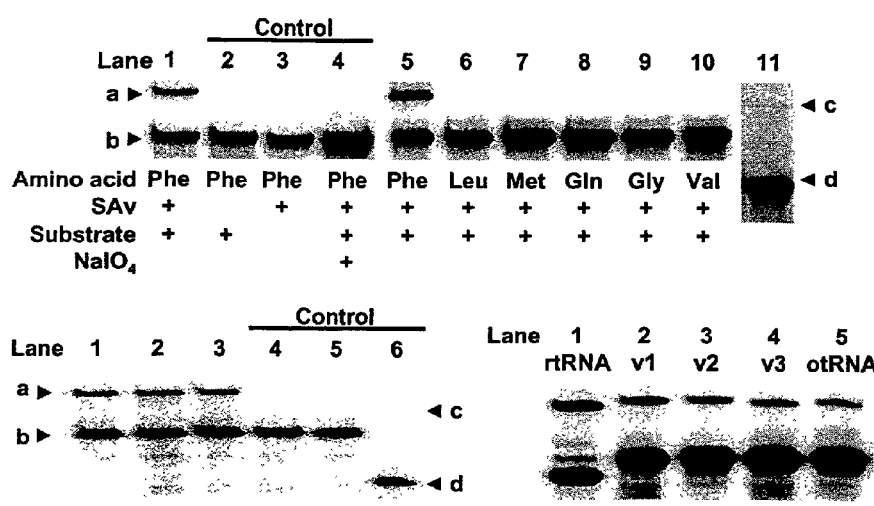
FIG. 4A is a representation of the self-aminoacylation activity and amino acid specificity of pre-24: a, Biotin-aminoacyl-pre-24 complexed with SAv; b, pre-24; c, Biotin-Phe-otRNA complexed with SAv; d, otRNA.
FIG. 4B is a representation of comparison of self-aminoacylation activity of pre-24 using three distinct esters. a, Biotin-Phe-pre-24 complexed with SAv; b, pre-24; c, Biotin-Phe-otRNA complexed with SAv; d, otRNA. Reactions were performed in the presence of 0.5 μM pre24 and 5 mM Phe-CME (lane 1), 5 mM Phe-AMP (lane 2), or 10 mM Phe-TE (lane 3) at 25° C. (lanes 1 and 3) or 0° C. (lane 2) for 30 min.
FIG. 4C is a representation of comparison of self-aminoacylation activity of pre-24 and its mutants containing different degrees of mutation and deletion in the tRNA domain. The wild-type pre-24 (lane 1) and pre-24$^{otRNA}$ (lane 5) contain the rtRNA and otRNA sequences of the tRNA domain, respectively.
Figure 6:
FIG. 6 shows aminoacylation states before and after mild base hydrolysis of aminoacyl-pre-24 with potassium carbonate. Lane 1–3: same as lanes 1–3 in FIG. 4A. Lane 4: Biotin-Phe-pre-24 RNA (same as RNA in lane 1) was treated with 50 mM K$_2$CO$_3$ for 15 min at 37° C. Lane 5: RNA recovered from lane 4 was used for aminoacylation under the same conditions as lane 1.

The self-aminoacylation activity was confirmed by the SAv-dependent mobility-gel-shift assay (FIG. 4A, lanes 1–3). Periodate oxidation completely eliminated activity, strongly suggesting that the aminoacylation site is the 3'-end (lane 4). Mild base hydrolysis of aminoacyl-pre-24 with potassium carbonate resulted in loss of the retarded band, i.e. Biotin-Phe was hydrolyzed from pre-24. When re-exposed to the aminoacyl substrate this deacylated pre-24 still showed full self-aminoacylation activity (see FIG. 6). This suggests that a 3' or 2'-ester bond is the only plausible linkage of the aminoacyl-pre-24.

The amino acid specificity of catalytic RNAs was investigated by using five distinct Biotin-aminoacyl-CMEs (FIG. 4, lanes 6–10). For substrates of Phe-CME, Phe-AMP and Phe-TE, self-aminoacylation reactions were carried out with the same procedures as those described as above, except that the aminoacyl-RNA pellet was resuspended in an acidic EPPS buffer (0.3 M, pH 5.5). 0.3 M EPPS-KOH was then added to this solution, which brought the pH to 8.0.

Reaction rates for these amino acids were drastically reduced compared with phenylalanine, indicating that the ribozyme domain has a remarkable specificity toward Biotin-Phe-CME.

Figure 7:
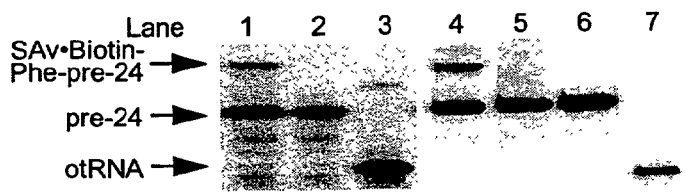
FIG. 7 shows aminoacylation of pre-24 and otRNA in the presence of Phe-AMP and Phe-TE. Lane 1: Aminoacylation of pre-24 in the presence of 5 mM Phe-AMP followed by biotinylation. Lane 2: Aminoacylation only. Lane 3: Aminoacylation of otRNA with 5 mM Phe-AMP followed by biotiylation. Lane 4: Aminoacylation of pre-24 in the presence of 10 mM Phe-TE followed by biotinylation. Lane 5: Aminoacylation only. Lane 6: Biotinylation only. Lane 7: Aminoacylation of otRNA with 10 mM Ohe-TE followe by biotinylation.

To further define the primary recognition element in the substrate, three synthetic phenylalanyl esters (FIG. 1C) were tested for activity (FIG. 4B) (16). Reactions were performed in the presence of 0.5 $\mu$M pre24 catalytic RNA and 5 mM Phe-CME (lane 1), 5 mM Phe-AMP (lane 2), or 10 mM Phe-TE (lane 3) at 25° C. (lanes 1 & 3) or 0° C. (lane 2) for 30 min. The absence of biotinylation (lane 4) or substrate (lane 5) for Phe-CME resulted in loss of the retarded band, indicating that the aminoacylation is necessary for the retarded band. The background aminoacylation was monitored using otRNA in the presence of 5 mM Phe-CME (lane 6). The same control experiments for Phe-AMP and Phe-TE were also performed (see FIG. 7). Omission of biotin from the a-amino group, i.e. Phe-CME, gave almost the same catalytic rate as that observed for Biotin-Phe-CME (FIG. 4B, lane 1) when the concentration of Phe-CME increased by 5-fold. This illustrates that the biotinyl group, presumably the amide functionality on the a-amino group, interacts with ribozyme, but it is not an essential element for substrate recognition. The ribozyme also accommodated the adenylate (Phe-AMP) and a thioester (Phe-TE) in place of the CME leaving group (lanes 2&3). This demonstrated that the critical recognition element of the substrate is the phenylalanyl side chain, not the leaving group.

EXAMPLE 4

This embodiment demonstrates the preparation and trans-aminoacylating activity of the catalytic RNA molecules. The pre-24 catalytic RNA from Example 1 and 2 was used in this illustration. First, pre-24 otRNA was subjected to RNase P scission (FIG. 5A) to liberate the 5'-catalytic domain from the 3'-tRNA domain. A [$^{32}$P]-body-labeled pre-24° tRNA was treated with RNase P RNA for 2 h, resulting in the cleavage of approximately 23% of pre-24$^{otRNA}$ (lane 1). The absence of RNase P yielded no cleaved product (lane 2). The marker RNAs (5$^1$-leader segment in lane 3 and otRNA in lane 4) were prepared by in vitro transcription using the corresponding DNA segments. *E. coli* RNase P RNA was in vitro transcribed using a PCR-amplified DNA template from the Ml gene of the pDW27 plasmid as previously described (Ziehler et a. (1996) *Biotechniques* 20, 622–624), then purified on 6% PAGE. The cleavage of pre-24$^{otRNA}$ (1 $\mu$M) by the RNase P RNA (1 $\mu$M) was carried out in I M NH$_4$OAc, 50 mM MgCl$_2$ and 0.1% SDS at 37° C. (14). After the reaction, the solution was ethanol-precipitated twice and the resulting solution was analyzed by 10% PAGE.

Figure 5A:
FIG. 5A is a representation of the trans-aminoacylation activity of the 5'-leader ribozyme. Cleavage of pre-24 otRNA by RNase P RNA. a, pre-24 otRIIA; b, 5' leader segment; c, otRNA.

Treatment of pre-24$^{otRNA}$ with *E. coli* RNase P RNA produced two fragments of lengths corresponding to the 5'-leader segment and the otRNA (FIG. 5A, lanes 1 and 2, compare with in vitro transcripts of each fragment in lanes 3 and 4). This demonstrates that pre-24$^{otRNA}$ is susceptible to RNase P RNA hydrolysis. Thus, the catalytically active pre-tRNA can be segmented tRNA-like molecule and a 5' leader segment.

Figure 1B:
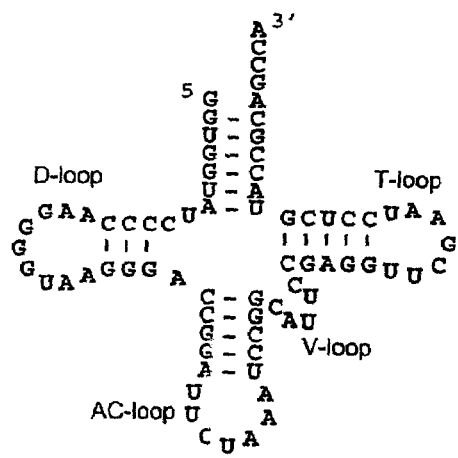
FIG. 1B is a representation of the Secondary structure of otRNA.
Figure 1C:
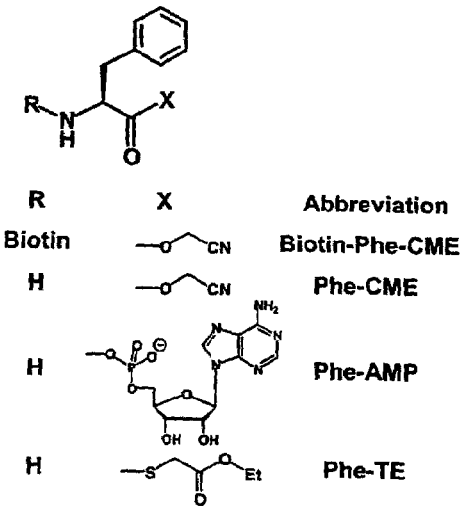
FIG. 1C is a representation of the chemical structure of substrates cyanomethyl ester (CME), adenosine monophosphate (AMP) (adenylate), and thioester (TE), respectively.
Figure 5B:
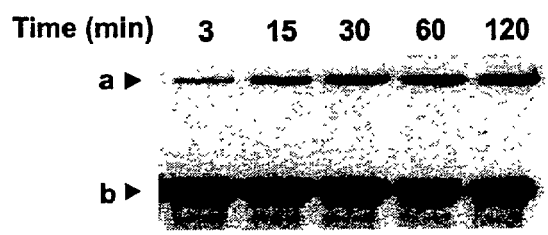
FIG. 5B is a representation of an autoradiogram showing the time course of 5'-leader ribozyme-catalyzed aminoacylation of otRNA. a, Biotin-Phe-otRNA complexed with SAv; b, otRNA. The RNase P-digested RNA fragments of pre-24$^{otRNA}$ were used for aminoacylation (k.b.=1.0 x10$^{-3}$ min$^{-1}$)

Next, it was examined whether the 5'-leader fragment could aminoacylate the otRNA fragment in trans (FIG. 1A, right). For the analysis of the trans-aminoacylation activity (FIG. 5B), an unlabeled pre-24$^{otRNA}$ was cleaved, and the individual segments of otRNA and 5'-leader domain were purified by 10%; PAGE. The tRNA segment was treated with calf intestinal alkaline phosphatase and then phosphorylated using T4 polynucleotide kinase in the presence of [$^{32}$P]-a-ATP. The 5'-leader and otRNA fragments generated by RNase P RNA action on pre-24$^{otRNA}$ were treated with Biotin-Phe-CME (FIG. 5B). The 5'-leader fragment transaminoacylated otRNA at a rate similar to the cis reaction of pre-24$^{otRNA}$. The in vitro transcribed 5'-leader fragment also exhibited trans-activity similar to that observed above. Thus, the RNase P RNA-digested 5' leader fragment can independently fold into its functional structure, and act as a trans-acting aminoacylation enzyme.

Figure 5C:
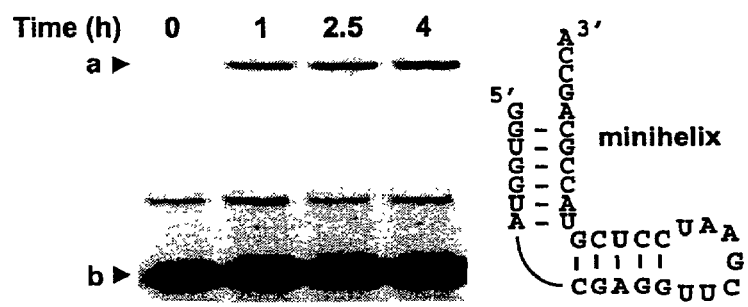
FIG. 5C is a representation of the time course of 5'-leader ribozyme-catalyzed aminoacylation of a minihelix RNA. a, Biotin-Phe-minihelix RNA complexed with SAv; b, minihelix RNA (SEQ ID NO:19) (consisting of the acceptor- T stem-loop region of otRNA).

The substrate properties of a minihelix RNA consisting of the acceptor- T stem-loop region of otRNA (FIG. 5C) were also tested. The 5'-leader ribozyme and minihelix RNA were in vitro transcribed, then purified on PAGE. Prior to the reaction, each of the RNAs (4 $\mu$M of 5' leader ribozyme and 3 $\mu$M of minihelix RNA) were folded independently. The remaining procedures were the same as described in the method section. The minihelix RNA was still aminoacylated by 5'-leader ribozyme, indicating that the anticodon loop is not essential for activity. An approximately 4-fold reduction of the observed rate as compared to otRNA, however, suggests that 5'-leader ribozyme interacts with additional elements present in the full-length of otRNA.

Figure 8:
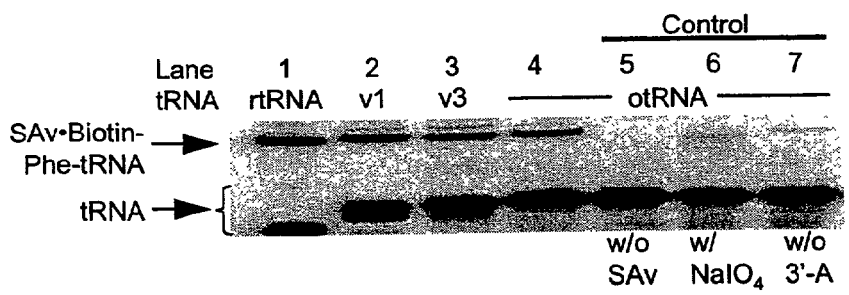
FIG. 8 shows ribozyme-catalyzed aminoacylation on tRNA variants in trans. Reactions were carried out for 3 hours. The v1 and v3 (lanes 2 and 3) are the fragment of the tRNA domain described in FIG. 4C.

Additionally, the 5'-leader fragment trans-aminoacylated otRNA at a rate similar to the cis reaction of pre-24$^{otRNA}$. The in vitro transcribed 5'-leader fragment also exhibited trans-activity similar to that observed above. In addition, this fragment showed activity toward rtRNA and its variants at similar rates to the respective cis reactions (FIG. 8).

In conclusion, the present invention provides modifed tRNAs with the ability to catalyze the aminoacylation of their own 3' ends. The 5$^1$-leader sequences may exist independently of the 3'-tRNA domains and still retain their catalytic property.

EXAMPLE 5

A scaffolding strategy was used for the selection of Leu-specific ribozymes using a 15'-mutagenized scaffold pool. The 15%-mutagenized scaffold RNA pool was synthesized as follows: Each nucleotide position of ribozyme, except for the 5'-primer region and the 5'-overlapped region of tRNA, is mutagenized on the corresponding DNA template by using an automated DNA synthesizer. Prior to the synthesis, each phosphoramidite base was mixed with the other three bases with the reactivity ratio of 85:5:5:5. The DNA template was synthesized according to the ribozyme sequence. The deprotection and purification of oligonucleotide was employed as standard methods. The DNA was amplified by the same method as described in Example 1, except that the PCR was carried out in a 200 $\mu$L scale. In vitro transcription of this DNA template followed by purification on PAGE gave the 15%-mutagenized scaffold RNA pool. After only five rounds of selection, active sequences appeared in the pool (whereas selection of pre-24$^{Phe}$ from a completely random pool required 15 rounds). It should be noted that the observed activity toward orthogonal tRNA (otRNA) is even higher than that of the original pre-24$^{Phe}$, indicating that this strategy is effective not only for switching the specificity but also for optimizing activity toward otRNA.

By using this approach, leucine specific cis aminoacylating RNAs were obtained. Two examples are presented as SEQ ID NO:17 and SEQ ID NO:18.

Although preferred embodiments of the present invention have been described and illustrated herein, the present invention is not limited to such preferred embodiments. Those skilled in the art will appreciate that various changes may be made without departing from the spirit of the invention.

The invention claimed is:

1. A method for identifying cis-aminoacylating catalytic RNA molecules comprising the steps of:
   a. providing tRNA molecules;
   b. providing ribozyme molecules;
   c. attaching the ribozyme molecules to the 5' end of the tRNA molecules to obtain a pool of ribozyme-tRNA molecules;
   d. contacting the ribozyme-tRNA molecules with an amino acid substrate wherein the amino acid substrate is selected from the group consisting of biotinyl-aminoacyl-cyanomethyl esters, aminoacyl-thio esters and aminoacyl-adenylates; and
   e. partitioning aminoacylated RNA molecules from non-aminoacylated RNA molecules wherein the aminoacylated RNA molecules are cis-aminoacylating catalytic RNA molecules aminoacylated with the amino acid substrate at the 3' end of the ribozyme-tRNA molecules.

2. The method of claim 1, wherein the tRNA molecule consists of SEQ ID NO: 16.

3. The method of claim 1, wherein the ribozyme domain molecule consists of SEQ ID NO: 9.

4. The method of claim 1 wherein the cis-aminoacylating catalytic RNA molecules consist of, from 5' to 3', SEQ 1N NO: 9, SEQ. ID NO: 16.

5. The method of claim 1 wherein the amino acid substrate is an N-biotinyl-L-aminoacyl-cyanomethyl-ester.

6. A method for identifying cis-aminoacylating catalytic RNA molecules comprising the steps of:
   a. providing RNA molecules having a tRNA domain and a 5'-leader ribozyme;
   b. contacting the RNA molecules with an amino acid substrate wherein the amino acid substrate is not conjugated to RNA selected from the group consisting of biotinyl-aminoacyl cyanomethyl esters, aminoacyl-thio esters and aminoacyl-adenylates; and
   c. partitioning aminoacylated RNA molecules from non-aminoacylated RNA molecules wherein the aminoacylated RNA molecules are cis-aminoacylating catalytic RNA molecules aminoacylated with the amino acid substrate at the 3' end of the ribozyme-tRNA molecules.

7. The method of claim 6 wherein the tRNA domain is SEQ ID NO: 16.

8. The method of claim 6 wherein the ribozyme is SEQ ID NO: 9.

9. The method of claim 6 wherein the amino acid substrate is an N-biotinyl-L-aminoacyl-cyanomethyl-ester.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 4482 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: Placenta
      (B) CLONE: 179527

(xi) SEQUENCE DESCRIPTION: SEQ ID NO:1:

```
CCACGCGTCC GGTTGCCAAC CCGCAGGCGA CTGGGCGCTT CATCCCACCC TCACCCCTTT      60

CCAGCCAAGG TGGCTGATCG GAGTCAGGCT CTCGAGGTCG CATTGCCACG AAACGGNGTG     120

TGTGAGCGCG TTGTCCCCGG NCCCCGGGGC CACTTCCCCT CGGCCTAGNA GACTGGACTG     180

GGGAAGGACG GGTCTGTTGT ACCCGGGAGG TGGAAGGAAA AGCCGAAAGC GGAGAAGTGT     240

GCGGGAGGGG AGTCTCCGCG CGGAGGNAGA CCGGNCTCCT CCAGTGCAGG TTGTGCGCTG     300

GGGAGCCAGC CASGGCAAAT GTTCTGAAAA AGACTCTGCA TGGGAATGGC CTGCCTTACG     360

ATGACAGAAA TGGAGGGAAC ATCCACCTCT TCTATATATC AGAATGGTGA TATTTCTGGA     420

AATGCCAATT CTATGAAGCA AATAGATCCA GTTCTTCAGG TGTATCTTTA CCATTCCCTT     480

GGGAAATCTG AGGCAGATTA TCTGACCTTT CCATCTGGGG AGTATGTTGG AGAAGAAATC     540

TGTATTGCTG CTTCTAAAGC TTGTGGTATC ACACCTGTGT ATCATAATAT GTTTGCTTTA     600

ATGAGTGAAA CAGAAAGGAT CTGGTATCCA CCCAACCATG TCTTCCATAT AGATGAGTCA     660

ACCAGGCATA ATGTACTCTA CAGAATAAGA TTTTACTTTC CTCGTTGGTA TTGCAGTGGC     720

AGCAACAGAG CCTATCGGCA TGGAATATCT CGAGGTGCTG AAGCTCCTCT TCTTGATGAC     780

TTTGTCATGT CTTACCTCTT TGCTCAGTGG CGGCATGATT TTGTGCATGG ATGGATAAAA     840

GTACCTGTGA CTCATGAAAC ACAGGAAGAA TGTCTTGGGA TGACAGTGTT AGATATGATG     900

AGAATAGCCA AGAAAACGA TCAAACCCCA CTGGCCATCT ATAACTCTAT CAGCTACAAG      960

ACATTCTTAC CACAATGTAT TCGAGCAAAG ATCCAAGACT ATCATATTTT GACAAGGAAG    1020

CGAATAAGGT ACAGATTTCG CAGATTTATT CAGCAATTCA GCCAATGCAA AGCCACTGCC    1080

AGAAACTTGA AACTTAAGTA TCTTATAAAT CTGGAAACTC TGCAGTCTGC CTTCTACACA    1140

GAGAAATTTG AAGTAAAAGA ACCTGGAAGT GGTCCTTCAG GTGAGGAGAT TTTTGCAACC    1200

ATTATAATAA CTGGAAACGG TGGAATTCAG TGGTCAAGAG GGAAACATAA AGAAAGTGAG    1260

ACACTGACAG AACAGGATTT ACAGTTATAT TGCGATTTTC CTAATATTAT TGATGTCAGT    1320

ATTAAGCAAG CAAACCAAGA GGGTTCAAAT GAAAGCCGAG TTGTAACTAT CCATAAGCAA    1380
```

```
GATGGTAAAA ATCTGGAAAT TGAACTTAGC TCATTAAGGG AAGCTTTGTC TTTCGTGTCA    1440

TTAATTGATG GATATTATAG ATTAACTGCA GATGCACATC ATTACCTCTG TAAAGAAGTA    1500

GCACCTCCAG CCGTGCTTGA AAATATACAA AGCAACTGTC ATGGCCCAAT TTCGATGGAT    1560

TTTGCCATTA GTAAACTGAA GAAAGCAGGT AATCAGACTG GACTGTATGT ACTTCGATGC    1620

AGTCCTAAGG ACTTTAATAA ATATTTTTTG ACTTTTGCTG TCGAGCGAGA AAATGTCATT    1680

GAATATAAAC ACTGTTTGAT TACAAAAAAT GAGAATGAAG AGTACAACCT CAGTGGGACA    1740

AAGAAGAACT TCAGCAGTCT TAAAGATCTT TTGAATTGTT ACCAGATGGA AACTGTTCGC    1800

TCAGACAATA TAATTTTCCA GTTACTAAA TGCTGTCCCC CAAAGCCAAA AGATAAATCA    1860

AACCTTCTAG TCTTCAGAAC GAATGGTGTT TCTGATGTAC CAACCTCACC AACATTACAG    1920

AGGCCTACTC ATATGAACCA AATGGTGTTT CACAAAATCA GAAATGAAGA TTTGATATTT    1980

AATGAAAGCC TTGGCCAAGG CACTTTTACA AAGATTTTTA AAGGCGTACG AAGAGAAGTA    2040

GGAGACTACG GTCAACTGCA TGAAACAGAA GTTCTTTTAA AAGTTCTGGA TAAAGCACAC    2100

AGGAACTATT CAGAGTCTTT CTTTGAAGCA GCAAGTATGA TGAGCAAGCT TTCTCACAAG    2160

CATTTGGTTT TAAATTATGG AGTATGTGTC TGTGGAGACG AGAATATTCT GGTTCAGGAG    2220

TTTGTAAAAT TTGGATCACT AGATACATAT CTGAAAAAGA ATAAAAATTG TATAAATATA    2280

TTATGGAAAC TTGAAGTTGC TAAACAGTTG GCATGGGCCA TGCATTTTCT AGAAGAAAAC    2340

ACCCTTATTC ATGGGAATGT ATGTGCCAAA AATATTCTGC TTATCAGAGA AGAAGACAGG    2400

AAGACAGGAA ATCCTCCTTT CATCAAACTT AGTGATCCTG GCATTAGTAT TACAGTTTTG    2460

CCAAAGGACA TTCTTCAGGA GAGAATACCA TGGGTACCAC CTGAATGCAT TGAAAATCCT    2520

AAAAATTTAA ATTTGGCAAC AGACAAATGG AGTTTTGGTA CCACTTTGTG GGAAATCTGC    2580

AGTGGAGGAG ATAAACCTCT AAGTGCTCTG GATTCTCAAA GAAAGCTACA ATTTTATGAA    2640

GATAGGCATC AGCTTCCTGC ACCAAAGTGG CAGAATTAG CAAACCTTAT AAATAATTGT    2700

ATGGATTATG AACCAGATTT CAGGCCTTCT TTCAGAGCCA TCATACGAGA TCTTAACAGT    2760

TTGTTTACTC CAGATTATGA ACTATTAACA GAAAATGACA TGTTACCAAA TATGAGGATA    2820

GGTGCCTTGG GGTTTTCTGG TGCCTTTGAA GACCGGGATC CTACACAGTT TGAAGAGAGA    2880

CATTTGAAAT TTCTACAGCA ACTTGGCAAG GGTAATTTTG GGAGTGTGGA GATGTGCCGG    2940

TATGACCCTC TACAGGACAA CACTGGGGAG GTGGTCGCTG TAAAAAAGCT TCAGCATAGT    3000

ACTGAAGAGC ACCTAAGAGA CTTTGAAAGG GAAATTGAAA TCCTGAAATC CCTACAGCAT    3060

GACAACATTG TAAAGTACAA GGGAGTGTGC TACAGTGCTG GTCGGCGTAA TCTAAAATTA    3120

ATTATGGAAT ATTTACCATA TGGAAGTTTA CGAGACTATC TTCAAAAACA TAAAGAACGG    3180

ATAGATCACA TAAAACTTCT GCAGTACACA TCTCAGATAT GCAAGGGTAT GGAGTATCTT    3240

GGTACAAAAA GGTATATCCA CAGGGATCTG GCAACGAGAA ATATATTGGT GGAGAACGAG    3300

AACAGAGTTA AAATTGGRGA TTTTGGGTTA ACCAAAGTCT TGCCACAAGA CAAAGAATAC    3360

TATAAAGTAA AAGAACCTGG TGAAAGTCCC ATATTCTGGT ATGCTCCAGA ATCACTGACA    3420

GAGAGCAAGT TTTCTGTGGC CTCAGATGTT TGGAGCTTTG GAGTGGTTCT GTATGAACTT    3480

TTCACATACA TTGAGAAGAG TAAAAGTCCA CCAGCGGAAT TTATGCGTAT GATTGGCAAT    3540

GACAAACAAG GACAGATGAT CGTGTTCCAT TTGATAGAAC TTTTGAAGAA TAATGGAAGA    3600

TTACCAAGAC CAGATGGATG CCCAGATGAG ATCTATATGA TCATGACAGA ATGCTGGAAC    3660

AATAATGTAA ATCAACGCCC CTCCTTTAGG GATCTAGCTC TTCGAGTGGA TCAAATAAGG    3720
```

-continued

```
GATAACATGG CTGGATGAAA GAAATGACCT TCATTCTGAG ACCAAAGTAG ATTTACAGAA    3780

CAAAGTTTTA TATTTCACAT TGCTGTGGAC TATTATTACA TATATCATTA TTATATAAAT    3840

CATGATGCTA GCCAGCAAAG ATGTGAAAAT ATCTGCTCAA AACTTTCAAA GTTTAGTAAG    3900

TTTTTCTTCA TGAGGCCACC AGTAAAAGAC ATTAATGAGA ATTCCTTAGC AAGGATTTTG    3960

TAAGAAGTTT CTTAAACATT GTCAGTTAAC ATCACTCTTG TCTGGCAAAA GAAAAAAAT    4020

AGACTTTTTC AACTCAGCTT TTTGAGACCT GAAARAATTA TTATGTAAAT TTTGCAATGT    4080

TAAAGATGCA CAGAATATGT ATGTATAGTT TTTACCACAG TGGATGTATA ATACCTTGGC    4140

ATCTTGTGTG ATGTTTAACA CACATGAGGG CTGGTGTTCA TTAATACTGT TTTCTAATTT    4200

TTCCATGGTT AATCTATAAT TAATTACTTC ACTAAACAAA CAAATTAAGA TGTTCAGATA    4260

ATTGAATAAG TACCTTTGTG TCCTTGTTCA TTTATATCGC TGGCCAGCAT TATAAGCAGG    4320

TGTATACTTT TAGCTTGTAG TTCCATGTAC TGTAAATATT TTTCACATAA AGGGAACAAA    4380

TGTCTAGTTT TATTTGTATA GGAAATTTGC CCTGACCCTA AATAATACAT TTGAAATGA    4440

AACAAGCTTA AAAAAAAAA AAAAAAAAA AAAAAAAAA AG    4482
```

(2) INFORMATION FOR SEQ ID NO:2:

(i) SEQUENCE CHARACTERISTICS:
        (A) LENGTH: 1132 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY:
        (B) CLONE:

(xi) SEQUENCE DESCRIPTION: SEQ ID NO:2:

```
Met Gly Met Ala Cys Leu Thr Met Thr Glu Met Glu Gly Thr Ser Thr
 1               5                  10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Gly
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Thr Val Leu Asp Met Met Arg Ile Ala Lys Glu
            180                 185                 190
```

```
Asn Asp Gln Thr Pro Leu Ala Ile Tyr Asn Ser Ile Ser Tyr Lys Thr
        195                 200                 205

Phe Leu Pro Gln Cys Ile Arg Ala Lys Ile Gln Asp Tyr His Ile Leu
        210                 215                 220

Thr Arg Lys Arg Ile Arg Tyr Arg Phe Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Ile Phe Ala Thr Ile
        275                 280                 285

Ile Ile Thr Gly Asn Gly Gly Ile Gln Trp Ser Arg Gly Lys His Lys
        290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
        355                 360                 365

Ile Asp Gly Tyr Tyr Arg Leu Thr Ala Asp Ala His His Tyr Leu Cys
    370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
        435                 440                 445

Tyr Lys His Cys Leu Ile Thr Lys Asn Glu Asn Glu Tyr Asn Leu
    450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
                485                 490                 495

Lys Cys Cys Pro Pro Lys Pro Lys Asp Lys Ser Asn Leu Leu Val Phe
            500                 505                 510

Arg Thr Asn Gly Val Ser Asp Val Pro Thr Ser Pro Thr Leu Gln Arg
        515                 520                 525

Pro Thr His Met Asn Gln Met Val Phe His Lys Ile Arg Asn Glu Asp
    530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
                565                 570                 575

Glu Val Leu Leu Lys Val Leu Asp Lys Ala His Arg Asn Tyr Ser Glu
            580                 585                 590

Ser Phe Phe Glu Ala Ala Ser Met Met Ser Lys Leu Ser His Lys His
        595                 600                 605

Leu Val Leu Asn Tyr Gly Val Cys Val Cys Gly Asp Glu Asn Ile Leu
```

-continued

```
            610                 615                 620
Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
                645                 650                 655

Leu Ala Trp Ala Met His Phe Leu Glu Glu Asn Thr Leu Ile His Gly
                660                 665                 670

Asn Val Cys Ala Lys Asn Ile Leu Leu Ile Arg Glu Glu Asp Arg Lys
                675                 680                 685

Thr Gly Asn Pro Pro Phe Ile Lys Leu Ser Asp Pro Gly Ile Ser Ile
690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
                740                 745                 750

Pro Leu Ser Ala Leu Asp Ser Gln Arg Lys Leu Gln Phe Tyr Glu Asp
                755                 760                 765

Arg His Gln Leu Pro Ala Pro Lys Trp Ala Glu Leu Ala Asn Leu Ile
                770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
                820                 825                 830

Ser Gly Ala Phe Glu Asp Arg Asp Pro Thr Gln Phe Glu Glu Arg His
                835                 840                 845

Leu Lys Phe Leu Gln Gln Leu Gly Lys Gly Asn Phe Gly Ser Val Glu
                850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
                900                 905                 910

Tyr Lys Gly Val Cys Tyr Ser Ala Gly Arg Arg Asn Leu Lys Leu Ile
                915                 920                 925

Met Glu Tyr Leu Pro Tyr Gly Ser Leu Arg Asp Tyr Leu Gln Lys His
                930                 935                 940

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
                980                 985                 990

Gly Asp Phe Gly Leu Thr Lys Val Leu Pro Gln Asp Lys Glu Tyr Tyr
                995                1000                1005

Lys Val Lys Glu Pro Gly Glu Ser Pro Ile Phe Trp Tyr Ala Pro Glu
    1010                1015                1020

Ser Leu Thr Glu Ser Lys Phe Ser Val Ala Ser Asp Val Trp Ser Phe
025                 1030                1035                1040
```

```
Gly Val Val Leu Tyr Glu Leu Phe Thr Tyr Ile Glu Lys Ser Lys Ser
            1045            1050             1055

Pro Pro Ala Glu Phe Met Arg Met Ile Gly Asn Asp Lys Gln Gly Gln
            1060            1065             1070

Met Ile Val Phe His Leu Ile Glu Leu Leu Lys Asn Asn Gly Arg Leu
        1075            1080             1085

Pro Arg Pro Asp Gly Cys Pro Asp Glu Ile Tyr Met Ile Met Thr Glu
        1090            1095             1100

Cys Trp Asn Asn Asn Val Asn Gln Arg Pro Ser Phe Arg Asp Leu Ala
105         1110            1115             1120

Leu Arg Val Asp Gln Ile Arg Asp Asn Met Ala Gly
            1125            1130
```

(2) INFORMATION FOR SEQ ID NO:3:

(i) SEQUENCE CHARACTERISTICS:
        (A) LENGTH: 1129 amino acids
        (B) TYPE: amino acid
        (C) STRANDEDNESS: single
        (D) TOPOLOGY: linear (xi) SEQUENCE DESCRIPTION: SEQ ID NO:3:

```
Met Gly Met Ala Cys Leu Thr Met Thr Glu Met Glu Ala Thr Ser Thr
1               5               10              15

Ser Pro Val His Gln Asn Gly Asp Ile Pro Gly Ser Ala Asn Ser Val
            20              25              30

Lys Gln Ile Glu Pro Val Leu Gln Val Tyr Leu Tyr His Ser Leu Gly
        35              40              45

Gln Ala Glu Gly Glu Tyr Leu Lys Phe Pro Ser Gly Glu Tyr Val Ala
50              55              60

Glu Glu Ile Cys Val Ala Ala Ser Lys Ala Cys Gly Ile Thr Pro Val
65              70              75              80

Tyr His Asn Met Phe Ala Leu Met Ser Glu Thr Glu Arg Ile Trp Tyr
            85              90              95

Pro Pro Asn His Val Phe His Ile Asp Glu Ser Thr Arg His Asp Ile
            100             105             110

Leu Tyr Arg Ile Arg Phe Tyr Phe Pro His Trp Tyr Cys Ser Gly Ser
        115             120             125

Ser Arg Thr Tyr Arg Tyr Gly Val Ser Arg Gly Ala Glu Ala Pro Leu
        130             135             140

Leu Asp Asp Phe Val Met Ser Tyr Leu Phe Val Gln Trp Arg His Asp
145             150             155             160

Phe Val His Gly Trp Ile Lys Val Pro Val Thr His Glu Thr Gln Glu
            165             170             175

Glu Cys Leu Gly Met Ala Val Leu Asp Met Met Arg Ile Ala Lys Glu
            180             185             190

Lys Asp Gln Thr Pro Leu Ala Val Tyr Asn Ser Val Ser Tyr Lys Thr
        195             200             205

Phe Leu Pro Lys Cys Val Arg Ala Lys Ile Gln Asp Tyr His Ile Leu
    210             215             220

Thr Arg Lys Arg Ile Arg Tyr Arg Phe Arg Arg Phe Ile Gln Gln Phe
225             230             235             240

Ser Gln Cys Lys Ala Thr Ala Arg Asn Leu Lys Leu Lys Tyr Leu Ile
            245             250             255

Asn Leu Glu Thr Leu Gln Ser Ala Phe Tyr Thr Glu Gln Phe Glu Val
```

-continued

```
                260                 265                 270
Lys Glu Ser Ala Arg Gly Pro Ser Gly Glu Ile Phe Ala Thr Ile
            275                 280                 285
Ile Ile Thr Gly Asn Gly Ile Gln Trp Ser Arg Gly Lys His Lys
            290                 295                 300
Glu Ser Glu Thr Leu Thr Glu Gln Asp Val Gln Leu Tyr Cys Asp Phe
305                 310                 315                 320
Pro Asp Ile Ile Asp Val Ser Ile Lys Gln Ala Asn Gln Glu Cys Ser
                325                 330                 335
Asn Glu Ser Arg Ile Val Thr Val His Lys Gln Asp Gly Lys Val Leu
            340                 345                 350
Glu Ile Glu Leu Ser Ser Leu Lys Glu Ala Leu Ser Phe Val Ser Leu
            355                 360                 365
Ile Asp Gly Tyr Tyr Arg Leu Thr Ala Asp Ala His His Tyr Leu Cys
            370                 375                 380
Lys Glu Val Ala Pro Pro Ala Val Leu Glu Asn Ile His Ser Asn Cys
385                 390                 395                 400
His Gly Pro Ile Ser Met Asp Phe Ala Ile Ser Lys Leu Lys Lys Ala
                405                 410                 415
Gly Asn Gln Thr Gly Leu Tyr Val Leu Arg Cys Ser Pro Lys Asp Phe
            420                 425                 430
Asn Lys Tyr Phe Leu Thr Phe Ala Val Glu Arg Glu Asn Val Ile Glu
            435                 440                 445
Tyr Lys His Cys Leu Ile Thr Lys Asn Glu Asn Gly Glu Tyr Asn Leu
            450                 455                 460
Ser Gly Thr Asn Arg Asn Phe Ser Asn Leu Lys Asp Leu Leu Asn Cys
465                 470                 475                 480
Tyr Gln Met Glu Thr Val Arg Ser Asp Ser Ile Ile Phe Gln Phe Thr
                485                 490                 495
Lys Cys Cys Pro Pro Lys Pro Lys Asp Lys Ser Asn Leu Leu Val Phe
            500                 505                 510
Arg Thr Asn Gly Ile Ser Asp Val Gln Ile Ser Pro Thr Leu Gln Arg
            515                 520                 525
His Asn Asn Val Asn Gln Met Val Phe His Lys Ile Arg Asn Glu Asp
530                 535                 540
Leu Ile Phe Asn Glu Ser Leu Gly Gln Gly Thr Phe Thr Lys Ile Phe
545                 550                 555                 560
Lys Gly Val Arg Arg Glu Val Gly Asp Tyr Gly Gln Leu His Lys Thr
                565                 570                 575
Glu Val Leu Leu Lys Val Leu Asp Lys Ala His Arg Asn Tyr Ser Glu
            580                 585                 590
Ser Phe Phe Glu Ala Ala Ser Met Met Ser Gln Leu Ser His Lys His
            595                 600                 605
Leu Val Leu Asn Tyr Gly Val Cys Val Cys Gly Glu Glu Asn Ile Leu
            610                 615                 620
Val Gln Glu Phe Val Lys Phe Gly Ser Leu Asp Thr Tyr Leu Lys Lys
625                 630                 635                 640
Asn Lys Asn Ser Ile Asn Ile Leu Trp Lys Leu Gly Val Ala Lys Gln
                645                 650                 655
Leu Ala Trp Ala Met His Phe Leu Glu Glu Lys Ser Leu Ile His Gly
            660                 665                 670
Asn Val Cys Ala Lys Asn Ile Leu Leu Ile Arg Glu Glu Asp Arg Arg
            675                 680                 685
```

-continued

```
Thr Gly Asn Pro Pro Phe Ile Lys Leu Ser Asp Pro Gly Ile Ser Ile
    690                 695                 700
Thr Val Leu Pro Lys Asp Ile Leu Gln Glu Arg Ile Pro Trp Val Pro
705                 710                 715                 720
Pro Glu Cys Ile Glu Asn Pro Lys Asn Leu Asn Leu Ala Thr Asp Lys
                725                 730                 735
Trp Ser Phe Gly Thr Thr Leu Trp Glu Ile Cys Ser Gly Gly Asp Lys
            740                 745                 750
Pro Leu Ser Ala Leu Asp Ser Gln Arg Lys Leu Gln Phe Tyr Glu Asp
        755                 760                 765
Lys His Gln Leu Pro Ala Pro Lys Trp Thr Glu Leu Ala Asn Leu Ile
    770                 775                 780
Asn Asn Cys Met Asp Tyr Glu Pro Asp Phe Arg Pro Ala Phe Arg Ala
785                 790                 795                 800
Val Ile Arg Asp Leu Asn Ser Leu Phe Thr Pro Asp Tyr Glu Leu Leu
                805                 810                 815
Thr Glu Asn Asp Met Leu Pro Asn Met Arg Ile Gly Ala Leu Gly Phe
            820                 825                 830
Ser Gly Ala Phe Glu Asp Arg Asp Pro Thr Gln Phe Glu Glu Arg His
        835                 840                 845
Leu Lys Phe Leu Gln Gln Leu Gly Lys Gly Asn Phe Gly Ser Val Glu
    850                 855                 860
Met Cys Arg Tyr Asp Pro Leu Gln Asp Asn Thr Gly Glu Val Val Ala
865                 870                 875                 880
Val Lys Lys Leu Gln His Ser Thr Glu Glu His Leu Arg Asp Phe Glu
                885                 890                 895
Arg Glu Ile Glu Ile Leu Lys Ser Leu Gln His Asp Asn Ile Val Lys
            900                 905                 910
Tyr Lys Gly Val Cys Tyr Ser Ala Gly Arg Arg Asn Leu Arg Leu Ile
        915                 920                 925
Met Glu Tyr Leu Pro Tyr Gly Ser Leu Arg Asp Tyr Leu Gln Lys His
    930                 935                 940
Lys Glu Arg Ile Asp His Lys Lys Leu Leu Gln Tyr Thr Ser Gln Ile
945                 950                 955                 960
Cys Lys Gly Met Glu Tyr Leu Gly Thr Lys Arg Tyr Ile His Arg Asp
                965                 970                 975
Leu Ala Thr Arg Asn Ile Leu Val Glu Asn Glu Asn Arg Val Lys Ile
            980                 985                 990
Gly Asp Phe Gly Leu Thr Lys Val Leu Pro Gln Asp Lys Glu Tyr Tyr
        995                 1000                1005
Lys Val Lys Glu Pro Gly Glu Ser Pro Ile Phe Trp Tyr Ala Pro Gln
    1010                1015                1020
Ser Leu Thr Glu Ser Lys Phe Ser Val Ala Ser Asp Val Trp Ser Phe
025                 1030                1035                1040
Gly Val Val Leu Tyr Glu Leu Phe Thr Tyr Ile Glu Lys Ser Lys Ser
                1045                1050                1055
Pro Pro Val Glu Phe Met Arg Met Ile Gly Asn Asp Lys Gln Gly Gln
            1060                1065                1070
Met Ile Val Phe His Leu Ile Glu Leu Leu Lys Ser Asn Gly Arg Leu
        1075                1080                1085
Pro Arg Pro Glu Gly Cys Pro Asp Glu Ile Tyr Val Ile Met Thr Glu
    1090                1095                1100
```

```
-continued

Cys Trp Asn Asn Asn Val Ser Gln Arg Pro Ser Phe Arg Asp Leu Ser
105             1110            1115            1120

Phe Gly Trp Ile Lys Cys Gly Thr Val
            1125

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

GGGCGGAAGT GCTCTCGGCG GAAG                                          24

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:5:

AGTGTGCTAC AGTGCTGGTC GTCG                                          24
```